(12) United States Patent
Notte et al.

(10) Patent No.: US 8,505,626 B2
(45) Date of Patent: Aug. 13, 2013

(54) α-AMINO ACID PHOSPHONIC ACID COMPOUNDS, METHOD OF PREPARATION OF USE THEREOF

(75) Inventors: Patrick Notte, Wavre (BE); Albert Devaux, Mont-Saint-Guiber (BE)

(73) Assignee: Dequest AG, Zug (CH)

( * ) Notice: Subject to any disclaimer, the term of this patent is extended or adjusted under 35 U.S.C. 154(b) by 40 days.

(21) Appl. No.: 12/376,899

(22) PCT Filed: May 25, 2007

(86) PCT No.: PCT/EP2007/004683
§ 371 (c)(1),
(2), (4) Date: May 11, 2009

(87) PCT Pub. No.: WO2008/017339
PCT Pub. Date: Feb. 14, 2008

(65) Prior Publication Data
US 2010/0186961 A1  Jul. 29, 2010

(30) Foreign Application Priority Data
Aug. 9, 2006  (EP) ..................................... 06016598

(51) Int. Cl.
*E21B 37/06* (2006.01)
*E21B 43/22* (2006.01)
*C09K 8/528* (2006.01)

(52) U.S. Cl.
USPC ........ 166/263; 166/279; 166/305.1; 166/310; 210/700; 252/175; 507/236; 507/237; 507/244; 562/11; 562/12

(58) Field of Classification Search
None
See application file for complete search history.

(56) References Cited

U.S. PATENT DOCUMENTS

| 4,080,375 | A | * | 3/1978 | Quinlan | 562/14 |
|---|---|---|---|---|---|
| 4,620,595 | A | * | 11/1986 | Schutt | 166/275 |
| 4,661,298 | A |  | 4/1987 | Mirviss et al. | |
| 5,112,496 | A | * | 5/1992 | Dhawan et al. | 210/700 |
| 5,261,491 | A | * | 11/1993 | Stewart et al. | 166/279 |
| 5,263,539 | A | * | 11/1993 | Salimi et al. | 166/279 |
| 5,362,899 | A | * | 11/1994 | Campbell | 558/108 |
| 5,414,112 | A |  | 5/1995 | Dragisich | |
| 5,776,875 | A | * | 7/1998 | Tang et al. | 510/247 |
| 5,858,244 | A | * | 1/1999 | Tang et al. | 210/698 |
| 7,429,575 | B2 |  | 9/2008 | Yu et al. | |
| 7,572,776 | B2 |  | 8/2009 | Yu et al. | |
| 7,776,844 | B2 |  | 8/2010 | Yu et al. | |
| 2004/0049287 | A1 | * | 3/2004 | Descouts et al. | 623/23.6 |
| 2004/0054422 | A1 | * | 3/2004 | Descouts et al. | 623/23.57 |
| 2007/0161543 | A1 | * | 7/2007 | Yu et al. | 514/7 |
| 2010/0247463 | A1 |  | 9/2010 | Yu et al. | |

FOREIGN PATENT DOCUMENTS

| DE | 3524502 | 7/1984 |
|---|---|---|
| GB | 1438079 | 6/1976 |
| GB | 2161468 | 1/1986 |
| WO | WO2007/082206 A2 | 7/2009 |

OTHER PUBLICATIONS

Studies in molecular structure and conformation of aminophosphonic acids: Crystal and molecular structure of N-phosphonomethyl-L-threonine, W. Sawka-Dobrowolska, T. Glowiak, J. Barycki; Journal of Crystallographic and Spectroscopic Research, vol. 19, No. 5, 1989.

* cited by examiner

*Primary Examiner* — George Suchfield
(74) *Attorney, Agent, or Firm* — Samuel Digirolamo; Husch Blackwell LLP

(57) ABSTRACT

Novel aminoacid alkylphosphonic acid compounds are disclosed. These compounds can be used in multiple applications, in particular in a scale inhibitor functionality in aqueous systems, including in marine oil recovery.

10 Claims, No Drawings

α-AMINO ACID PHOSPHONIC ACID COMPOUNDS, METHOD OF PREPARATION OF USE THEREOF

CROSS REFERENCE TO RELATED APPLICATIONS

This Application is a U.S. National Phase patent application of International Application PCT/EP 2007/004683, filed 25 May 2007, which claims the benefit of priority from European Patent Application No. 06016598.2 filed on 9 August 2006. The disclosures of International Application No. PCT/EP2007/004683 and European Patent Application No. 06016598.2 are incorporated herein by reference.

This invention relates to novel α-amino acid phosphonic acid compounds embodying selected amino acids, namely arginine, histidine, iso-leucine, leucine, methionine, threonine and phenylalanine wherein available N—H groups have been reacted to yield an alkylphosphonic acid moiety. Also disclosed is a method of making the novel compounds and the beneficial application of such compounds.

The compounds in accordance with the invention can be used beneficially in multiple industrial and other, non-exhaustively listed, applications including water-treatment, scale inhibition, dispersion, sequestration, corrosion inhibition, pharmaceutical and pharmaceutical intermediates, textiles, detergents, secondary oil recovery, paper industry, sugar and beer industry, fertilizers and micronutrients and metal treatment.

A-Amino acids (amino acids) are eminently well known and have been applied for a very long time. Such amino acids are found as natural products, as such, or as proteins which upon hydrolysis can yield amino acids or, usually, mixtures of such amino acids. Such amino acids can also be synthesized by methods well known in the art. Significant quantities of individual amino acids are actually commercialized in numerous territories for a multitude of established applications. As one can accordingly expect, the prior art concerning amino acids broadly is very substantial indeed.

Phosphonomethylene aminocarboxylates are described in GB 1 438 079. U.S. Pat. No. 4,661,298 describes a process for the formation of phosphonoalkylated aminoacids by reacting cysteine with a haloalkylphosphonic acid in the presence of a catalytically effective amount of a polyamine catalyst. German patent application DE 3524502 discloses effective scale inhibitor systems containing (phosphonomethylene)-aminomethylene carboxylic acid. The latter acid can be prepared starting from glycin. GB 2 161 468 also contemplates using comparable amino acid phosphonate compounds for scale control. N-phosphonomethyl-L-threonine is known from Journ. Of Crystallographic and Spectroscopic Research (1989), 19(5), 861-71.

U.S. Pat. No. 5,414,112 discloses N-bis(phosphonomethyl)amino acids and their use to control calcium carbonate scale in contact with industrial process waters. Specific compounds described are N,N-bis(phosphonomethyl)-L-glutamic acid, N,N-bis(phosphonomethyl)-L-serine and N,N,N',N'-bis(phosphonomethyl)-L-lysine. The L-lysine compound is represented by species carrying one phosphonomethyl moiety attached to one amino radical. WO 2006/074730 describes a process for the manufacture of aminoalkylene phosphonic acid compounds starting from phosphorous acid, an amine and a formaldehyde in the presence of a heterogeneous Broensted acid catalyst.

It is an object of this invention to provide novel phosphonate compounds capable of beneficial use in a variety of industrial applications. It is a further object of this invention to make available novel phosphonate compounds capable of generating beneficial, at least equivalent, performance compared to extant aminoalkylene phosphonic acids. Yet another object of this invention aims at discovering phosphonate compounds providing superior performance per ponderal unit of phosphonic acid moiety. An additional object aims at creating new compounds capable of delivering desirable synergistic application performance as compared to what results from the use of the individual reaction partners and/or comparable art structures.

The foregoing and other objects can now be met by the provision of narrowly defined amino acid phosphonates.

The term "percent" or "%" as used in the description stand, unless defined differently for "percent by weight" or "% by weight". The term "amino acid" as used in the description and the claims stands for "α-amino acid". The terms "phosphonic acid" and "phosphonate" are also used interchangeably depending, in a known manner, upon medium prevailing alkalinity/acidity conditions. The term "ppm" stands for "parts per million". The term "threshold" is well known in the water treatment domain. The ability of very small amounts of scale inhibitors to keep large quantities of scalants in solution is known as the "threshold effect". Or in other words, it is the prevention of precipitation from supersaturated solutions of scalants by ppm levels of inhibitor.

Novel amino acid phosphonate compounds have now been discovered which can meet the objects of the invention. In more detail this invention concerns aminoacid phosphonic acid compound having the general formula:

wherein A is an α-amino acid moiety selected from the group of: arginine; histidine; iso-leucine; leucine; methionine; threonine; and phenylalanine; and wherein B is an alkylphosphonic acid moiety having from 1 to 6 carbon atoms in the alkylgroup;

with the proviso that x is an integer of from 1 to 6 in the event the amino acid moiety is arginine and from 1 to 3 in the event the amino acid moiety is histidine and x is 2 in the event the amino acid moiety is selected from leucine, iso-leucine, methionine, threonine and phenylalanine.

A first essential moiety in the novel compounds of this invention is represented by selected α-amino acids, namely arginine, histidine, leucine, isoleucine, methionine, threonine and phenylalanine. Amino acids generally are the building blocks of proteins. There are over forty known amino acids about twenty of which are actually contained in animal tissue. Amino acids can be made by hydrolysis starting from proteins, by enzymatic fermentation and/or by chemical synthesis. This domain of the technology is eminently well known and all the individual technologies are abundantly documented in the literature.

Natural methionine in proteins is present as the optically active L-isomer. Mixtures of D- and L-optical isomers can be produced by known chemical processes and the individual isomers can be separated. D,L-methionine can be synthesized, in a known manner, starting from acrolein.

Arginine is also produced in industrial quantities and is used commercially in pharmaceuticals, dietary supplements, functional beverages and personal care products. Phenylalanine is widely available and is used for the manufacture of e.g. aspartame and for pharmaceutical purposes. Threonine is produced in major quantities and is used in a variety of applications including pharmaceuticals. Histidine is commercially available and used in e.g. the pharmaceutical industry. Isoleucine and leucine are small-volume amino acids which have found application in nutritional formulas, in pharmaceuticals, dietary supplements and (leucine) as a lubricant in aspartame tablets.

The novel amino acid phosphonates of this invention can be made by reacting one or more of the N—H functions of the amino acid with phosphorous acid under addition of formaldehyde, in the presence of hydrochloric acid, in aqueous medium having a pH of generally less than 4 by heating that reaction mixture, at a temperature of usually greater than 70° C. for a sufficient time to complete the reaction. This kind of reaction is conventional and well-known in the domain of the technology and examples of the novel phosphonate compounds have been synthesized, as described below, via the hydrochloric acid route.

In preferred method, the aminoacid phosphonates can be made under substantial exclusion of hydrohalogenic acid and corresponding by-products and intermediates. Specifically, the aminoacid phosphonates can be manufactured in presence of not more than 0.4%, preferably less than 2000 ppm, of hydrohalogenic acid, expressed in relation to the phosphorous acid component (100%) by reacting:
(a) phosphorous acid;
(b) an aminoacid; and
(c) a formaldehyde:
in reactant ratios of (a): (b) of from 0.05:1 to 2:1; (c): (b) of from 0.05:1 to 5:1; and (c): (a) of from 5:1 to 0.25:1;
wherein (a) and (c) stand for the number of moles to be used and (b) represents the number of moles multiplied by the number of N—H functions in the amine, in the presence of an
acid catalyst having a pKa equal or inferior to 3.1, said catalyst being homogeneous with respect to the reaction medium and being used in reactant ratios as follows:

(b):(d) of from 40:1 to 1:5;

wherein (d) stands for the number of moles of catalyst multiplied by the number of available protons per mole of catalyst, followed by recovering the aminoacid phosphonates formed in a manner known per sé. The term "homogeneous" catalyst means that the catalyst, suitable for use, forms a single liquid phase within the reaction medium under the reaction conditions. The homogeneous nature of a catalyst can be ascertained routinely by e.g. visible inspection of precipitation or phase separation properties.

Preferred catalyst species can be selected from trifluoroacetic acid, trifluoromethane sulfonic acid, methane sulfonic acid, oxalic acid, malonic acid, p-toluene sulfonic acid and naphthalene sulfonic acid.

The homogenous reaction is preferably conducted at a temperature in the range of from 70° C. to 150° C. with an approach selected from:
  conducting the reaction under ambient pressure with or without distillation of water and non-reacted formaldehyde;
  in a closed vessel under autogeneous pressure built up;
  in a combined distillation and pressure arrangement whereby the reaction vessel containing the reactant mixture is kept under ambient pressure at the reaction temperature followed by circulating the reaction mixture through a reactor operated under autogeneous pressure built up thereby gradually adding the formaldehyde and other selected reactants in accordance with needs; and
  a continuous process arrangement, possibly under autogeneous pressure built up, whereby the reactants are continuously injected into the reaction mixture and the phosphonic acid reaction products is withdrawn on a continuous basis.

In another preferred method, the aminoacid phosphonates for use herein can be prepared under substantial exclusion of hydrohalogenic acid, specifically in the presence of not more than 0.4%, preferably less than 2000 ppm, of hydrohalogenic acid, expressed in relation to the phosphorous acid component (100%), by reacting: (a) phosphorous acid; (b) an aminoacid; and (c) formaldehyde; in reactant ratios as follows: (a): ((b) of from 0.05:1 to 2:1; (c): (b) of from 0.05:1 to 5:1; and (c): (a) of from 5:1 to 0.25:1; wherein (a) and (c) stand for the number of moles to be used and (b) represents the number of moles multiplied by the number of N—H functions in the amino acid, in the presence of a heterogeneous, with respect to the reaction medium, Broensted acid catalyst selected from the group consisting of:
(1) solid acidic metal oxide combinations as such or supported onto a carrier material;
(2) cation exchange resins selected from the group comprising copolymers of styrene, ethyl vinyl benzene and divinyl benzene, functionalized so as to graft $SO_3H$ moieties onto the aromatic group and perfluorinated resins carrying carboxylic and/or sulfonic acid groups;
(3) organic sulfonic and carboxylic Broensted acids which are substantially immiscible in the reaction medium at the reaction temperature;
(4) an acid catalyst derived from:
  (i) the interaction of a solid support having a lone pair of electrons onto which is deposited an organic Broensted acid;
  (ii) the interaction of a solid support having a lone pair of electrons onto which is deposited a compound having a Lewis acid site;
  (iii) heterogeneous solids functionalized by chemical grafting with a Broensted acid group or a precursor therefore; and
(5) heterogeneous heteropolyacids of the general formula $H_xPM_yO_z$ wherein P is selected from phosphorus and silicon and M is selected from W and Mo and combinations thereof
followed by recovering the aminoacid alkylphosphonic acid formed in a manner known per sé.

Examples of suitable Broensted catalysts are fluorinated carboxylic acids and fluorinated sulfonic acids having from 6 to 24 carbon atoms in the hydrocarbon chain. A specific example of a suitable catalyst is represented by perfluorinated undecanoic acid. In another execution, suitable heterogeous acid catalysts can be represented by cation exchange resins. Usually such resins comprise copolymers of styrene, ethylvinyl benzene and divinyl benzene functionalized such as to graft $SO_3H$ groups onto the aromatic groups.

The heterogeneous Broensted catalyst can be used in many operational manufacturing arrangements well known in the domain of the technology. The term "heterogeneous" means that the Broensted catalyst is substantially insoluble in the reaction medium at the reaction conditions or substantially immiscible, thus liquid, in the reaction medium at the reaction conditions. The heterogeneous reaction is preferably conducted at a temperature in the range of from 70 to 150° C. for a time sufficient to complete the reaction.

The phosphorous acid reactant is preferably prepared, in a known manner, under substantial exclusion of halogen, by contacting elemental phosphorus, such as tetraphosphorus, with water at a temperature below 200° C., in the presence of a catalyst effective to promote oxidation of phosphorus, by reaction with water; or by contacting P(V) species with a reducing agent, such as hydrogen, in the presence of a reducing catalyst; or by contacting a hydrolysis feed mixture comprising phosphate esters and phosphonate esters with liquid water and steam to thereby hydrolyze the phosphonate esters to phosphorous acid.

The essential formaldehyde component is a well known commodity ingredient. Formaldehyde generally is produced and sold as water solutions containing variable, frequently minor, e.g. 0.3-3%, amounts of methanol and are reported on a 37% formaldehyde basis. Formaldehyde solutions exist as a mixture of oligomers. Formaldehyde precursors can, for example, be represented by paraformaldehyde, a solid mixture of linear poly(oxymethylene glycols) of usually fairly short, n=8-100, chain length, and cyclic trimers and tetramers of formaldehyde designated by the terms trioxane and tetraoxane respectively. The formaldehyde component can also be represented by aldehydes and ketones having the formula $R_1R_2C=O$ wherein $R_1$ and $R_2$ can be identical or different and are selected from the group of hydrogen and organic radicals. When $R_1$ is hydrogen, the material is an aldehyde. When both $R_1$ and $R_2$ are organic radicals, the material is a ketone. Species of useful aldehydes are, in addition to formaldehyde, acetaldehyde, caproaldehyde, nicotinealdehyde, crotonaldehyde, glutaraldehyde, p-tolualdehyde, benzaldehyde, naphthaldehyde and 3-aminobenzaldehyde. Suitable ketone species for use herein are acetone, methylethylketone, 2-pentanone, butyrone, acetophenone and 2-acetonyl cyclohexanone.

A number of amino acid phosphonates are thus made available as follows.

| Amino Acid (AA) | Number of Phosphonates/AA | |
|---|---|---|
| | As claimed | Preferred |
| Arginine | 1-6 | 2-6 |
| Histidine | 1-3 | 2-3 |
| Leucine | 2 | |
| Isoleucine | 2 | |
| Methionine | 2 | |
| Threonine | 2 | |
| Phenylalanine | 2 | |

The syntheses of some of the novel α-amino acid phosphonates herein are described.

165.19 g (1 mole) of L-phenyl alanine are mixed with a solution of 164 g (2 moles) of phosphorous acid in 147.8 g of 37% aqueous hydrochloric acid (1.5 moles) and 250 cc of water. The mixture is heated under stirring to 110° C. 180.5 g of a 36.6% aqueous solution (2.2 moles) of formaldehyde are added over a period of 110 minutes while maintaining the reaction temperature between 106° C. and 107° C. Upon completion of the formaldehyde addition, the reaction mixture is maintained, for an additional 90 minutes, at a temperature of 107° C. to 108° C. $^{31}P$ NMR analysis of the crude product showed the presence of 68% of L-phenyl alanine bis(methylene phosphonic acid).

131.17 g (1 mole) of L-isoleucine are mixed with a solution of 164 g (2 moles) of phosphorous acid in 147.8 g of 37% aqueous hydrochloric acid (1.5 moles) and 150 cc of water. The mixture is heated under stirring to 110° C. 180.5 g of a 36.6% aqueous solution of formaldehyde (2.2 moles) are added over a period of 100 minutes while maintaining the reaction temperature at 110° C. Upon completion of the formaldehyde addition, the reaction mixture is maintained at 110° C. for an additional 110 minutes. $^{31}P$ NMR analysis of the crude product showed the presence of 69.7% of L-isoleucine bis(methylene phosphonic acid).

131.17 g (1 mole) of D,L-leucine are mixed with a solution of 164 g (2 moles) of phosphorous acid in 147.8 g of aqueous hydrochloric acid (1.5 moles) and 150 cc of water. The mixture is heated, under stirring, to 105° C. 180.5 g of a 36.6% aqueous solution of formaldehyde (2.2 moles) are then added over a period of 100 minutes while maintaining the reaction temperature between 105° C. and 110° C. Upon completion of the formaldehyde addition, the reaction mixture is maintained at 110° C. for an additional 60 minutes. $^{31}P$ NMR analysis of the crude product showed the presence of 69.7% of D,L-leucine bis(methylene phosphonic acid).

Arginine was reacted, in a conventional manner, with phosphorous acid and formaldehyde in the presence of hydrochloric acid. The crude reaction was found to be substantially completely, 72.7%, represented by a bis(alkylene phosphonic acid) derivative. This reaction product was used in the Examples.

The aminoacid phosphonic acid compounds of this invention were found to be particularly suitable for scale control, such as barium and strontium scale and calcium carbonate and other alkaline earth metal scale, and can be useful and desirable for application in water treatment broadly, including application in connection with water treatment systems and oil recovery.

Scale formation, such as carbonate and sulphate scales, can be a major problem in oil field production facilities that can result in a significant well productivity decline. This can, in particular, apply when sea water is injected into the oil bearing formation to compensate e.g. for a loss in gas pressure. As a result of the presence of important quantities of barium and calcium ions in the down-hole formation water, calcium sulphate and especially barium sulphate and strontium sulphate can become a major problem in the operation of the well. Whereas sulphate scales prevail upon seawater injection during the enhanced oil recovery treatment, milder pH conditions, prevailing closer to the surface, pressure differences and high temperatures in the down-hole formation usually lead to the formation of mixtures of carbonate and sulphate scale. The scale inhibitors shall therefore exhibit performance over a broad range of conditions such as can occur in the oil wells and production facilities. The inhibitor can be introduced into the oil bearing formation by any suitable treatment including a "squeeze" treatment. In general such a method for oil recovery requires injecting into a marine oil well an aqueous solution of the aminoacid phosphonic acid scale inhibitor of this invention in a usual level of from 0.1 to 100000 ppm. Frequently, the production oil well activity is stopped and the inhibitor solution is injected into the oil well formation. It was established that the scale inhibitors in accordance with this invention can be used effectively and singly. The squeeze treatment generally consists of injecting a scale inhibitor solution into the wellbore of the producing well to place the inhibitor into the formation. The scale inhibitor released from the formation is present, in the return water, in a concentration of, at least, 0.1, usually at least 0.5, frequently from 10 to 100 ppm to thus exhibit effective scale control and consequently secure oil well production continuity with levels of inhibitor means reduced by one order of magnitude compared to actually prevailing practice.

In more detail, a beneficial method for oil recovery can be done by injecting into marine oil wells an aqueous solution of the aminoacid phosphonic acid compound of the invention in a level of from 0.1 to 100000 ppm. The method can be conducted by continuously injecting into the well an aqueous solution of from 0.1 to 800 ppm of the aminoacid phosphonic acid compound. The continuous injection frequently means that the scale inhibitor solution is injected into the water injection well. However, it is understood that the continuous injection can also apply to the surroundings of the production well such as the well-head arrangement including underwater equipment for example pumps and pipes. The aminoacid scale inhibitors of this invention can also be used in squeeze oil recovery methods. Such squeeze method comprises, in sequence: stopping the production wellbore activity; introducing through the production wellbore the aqueous treatment solution containing the aminoacid phosphonic acid scale inhibitor in a level of from 100 to 100000 ppm; injecting sea water through the production wellbore to place the scale inhibitor within the targeted area of the formation; restarting the oil extraction activity; and producing return fluids, containing oil and return water, through the production wellbore.

The aminoacid phosphonic acid inhibitors in accordance with this invention can also be used beneficially in scale forming water systems containing usually more than 100 mg/l of barium and/or strontium hardness and/or calcium carbonate and having a pH generally within the range of from 2-10. To that effect, of from 0.1 to 800 ppm, preferably of from 0.2 to 100 ppm, of the aminoacid phosphonate scale inhibitor is added to the scale forming water system.

The individual aminoacid phosphonate scale inhibitors can, in one execution, be used substantially singly, or in the event they are used as a mixture of more than one individual species then it was observed that one individual inhibitor in accordance with this invention shall constitute, on a ponderal basis, at least 50%, usually 60% or more of the mixture of inhibitors of this invention. It was observed that aminoacid mixtures originating from protein hydrolysates are not well suitable for use in the method herein due, inter alia, to interactions of the various species which can adversely affect performance. Preferred scale inhibitors herein, particularly for application within the context of oil producing wells, shall have a thermal decomposition, measured at 140° C., of less than about 10%.

In one preferred execution herein, the scale inhibitor for use in the method aspect of this invention can be represented by selected combinations of the inventive aminoacid polyphosphonates in combination with a phosphonic acid selected from the group of: (a) amino(poly)alkylene polyphosphonic acids wherein the alkylene moiety contains from 1 to 20 carbon atoms; (b) hydroxyalkylene polyphosphonic acids wherein the alkylene moiety contains from 2 to 50 carbon atoms; and (c) phosphono alkane polycarboxylic acids wherein the alkane moiety is in straight chain configuration containing from 3 to 12 carbon atoms. Actually preferred are: aminoalkylene polyphosphonic acids having from 1 to 12 carbon atoms in the alkylene moiety; hydroxyalkylene phosphonic acids containing from 2 to 12 carbon atoms in the alkylene moiety and two phosphonic acid groups; whereas phosphono alkane polycarboxylic acids have a straight chain alkane configuration having from 4 to 8 carbon atoms and wherein the molar ratio of phosphonic acid radical to carboxylic acid radical is in the range of from 1:2 to 1:4. Particularly preferred are polyphosphonic acids having from 2 to 8 phosphonic acid groups. Individually preferred species include the following: aminotri(methylene phosphonic acid) and its N-oxide; 1-hydroxyethylene(1,1-diphosphonic acid); ethylenediamine tetra(methylene phosphonic acid); diethylene triamine penta(methylenephosphonic acid); hexamethylene diamine tetra(methylene phosphonic acid); hydroxyethyl aminobis(methylene phosphonic acid); N,N'-bis(3-aminopropyl)-ethylenediamine hexa(methylene phosphonic acid); and butane-2-phosphono-1,2,4-tricarboxylic acid.

The ponderal ratio of aminoacid phosphonate to phosphonic acid is in the range of from 98:2 to 25:75, preferably from 90:10 to 50:50.

The scale inhibitor performance of the novel aminoacid alkyl phosphonates of this invention can be quantified thereby using comparative testing methods as follows.

Thermal Stability Assessment.

This is a test to assess the thermal stability of phosphonates in the presence of synthetic North Sea water. The test is carried out by submitting mixtures of North Sea water and phosphonates stabilized at pH 5.5 to a one week heating at 140° C. The thermal degradation is determined by $^{31}$P NMR analysis. The results give the percentage by weight of product which is decomposed after the treatment.

Test details are as follows:
prepare an aqueous solution containing 20% of active acid phosphonate (AA) at pH 5.5 (solution 1);
prepare synthetic North Sea water having a pH of 5.5 (solution 2);
prepare a sample of 1% active acid phosphonate by mixing 1 g of solution 1 with 19 g of solution 2;
put the sample so prepared in an oven at 140° C. for one week; and
analyze the sample, after the heat treatment, for thermal decomposition by means of $^{31}$P NMR spectroscopy.

Brine/Sea Water Compatibility.

This test assesses sea water compatibility of the phosphonates added at: 100; 1000; 10000; and 50000 ppm to North Sea water after 22 hours at 95° C. Calcium left in solution is measured by ICP.

Test details are as follows:
prepare synthetic North Sea water at pH 5.5;
add the phosphonate at 0, 100, 1000, 10000 and 50000 ppm active acid to the synthetic North Sea water solution;
prepare 5 blank solutions made by mixing the required amount of distilled water with North Sea water to obtain the same dilution as obtained by the addition of 1, 100, 1000, 10000 and 50000 ppm active acid phosphonate to the synthetic North Sea water solution;
the phosphonate samples with the respective phosphonates at the 4 concentrations as well as the 5 blanks are stored in an oven at 95° C. for a period of 22-24 hours;
upon completion of the test, the samples are observed visually;
after completion of the test, the pH values are being carefully monitored and 50 ml are drawn from each sample, filtered through a 40 um Millipore filter and stabilized at pH<2 by addition of 37% aqueous hydrochloric acid;
Ca tolerance values are calculated as follows:

$$\% \text{ Ca tolerance} = \frac{V_1}{V_0} \times 100$$

where $V_0$=ppm Ca found in the blank solution; and
$V_1$=ppm Ca found in the solution with the phosphonate.

Barium Sulphate Scale Inhibition.

This is a static test to evaluate the efficiency of phosphonates in preventing barium and strontium scale inhibition in oil field scaling conditions. The test is carried out by determining the amount of $BaSO_4$ and $SrSO_4$ that has precipitated after 22 hours at 90° C. in a 50/50 mixture of synthetic North Sea water and Formation water containing the phosphonates to be tested at 5 different concentrations. The amount of soluble Ba and Sr ions is determined by ICP. The results stand for the minimum phosphonate concentration for 100% barium sulphate scale inhibition or give the scale inhibition at 100 ppm loading of phosphonate.

Test details are as follows:

Synthetic North Sea water:

| Salts | mmol/l |
|---|---|
| NaCl | 420.1 |
| CaCl$_2$•2H$_2$O | 10.08 |
| MgCl$_2$•6H$_2$O | 54.32 |
| KCl | 8.7 |
| Na$_2$SO$_4$•10H$_2$O | 25.8 |
| NaHCO$_3$ | 2.21 |

Formation water:

| Salts | mmol/l |
|---|---|
| NaCl | 1313 |
| CaCl$_2$•2H$_2$O | 77.75 |
| MgCl$_2$•6H$_2$O | 19.74 |
| KCl | 11.0 |
| BaCl$_2$•2H$_2$O | 1.82 |
| SrCl$_2$•6H$_2$O | 7.53 | synthetic North Sea and Formation water are prepared having a pH of 6. These water solutions are preheated at 90° C. before starting the test. An acetic acid/sodium acetate buffer is prepared and added to the North Sea water in order to give the required pH;

add to a glass bottle the required amount of scale inhibitor to obtain the test concentrations (15, 30, 50, 70 and 100 ppm active phosphonic acid) of the scale inhibitor in the final test mixture;

to this glass bottle, add 50 ml of North Sea water while stirring. Then add to this glass bottle 50 ml of Formation water;

also prepare one blank solution by mixing 50 ml of North Sea water with 50 ml of Formation water;

put the sample bottles in an oven for 22 hours at 90° C.;

after 22 hours, take 3 ml of each test solution from the surface, filter through a 0.45 µm Millipore filter and add to a stabilizing solution. The samples are then analyzed by ICP for Ba and Sr;

the phosphonate efficiencies as BaSO$_4$ and SrSO$_4$ scale inhibition are calculated as follows:

$$\% \text{ Scale inhibition} = \frac{V_1 - V_0}{V_2 - V_0} \times 100$$

where $V_0$=ppm Ba (or Sr) found in the blank solution;

$V_1$=ppm Ba (or Sr) found in the solution with the inhibitor;

$V_2$=ppm Ba (or Sr) present in the original solution.

Scale inhibitor phosphonate samples for use in the method of this invention were performance tested by means of the foregoing testing procedures. The performance data were as follows.

EXAMPLES

| N° | Amino Acid | Ba Scale Inhibition(*) | Ca Tolerance in % | | | |
|---|---|---|---|---|---|---|
| | | | 100 | 1000 | 10000 | 50000(**) |
| 1 | L-phenyl alanine | 10 ppm full scale | 96 | 76 | 1 | 26 |
| 2 | L-isoleucine | 85% @ 100 ppm | 93 | 96 | 44 | 82 |
| 3 | L-histidine | 90% @ 100 ppm | 100 | 100 | 95 | 100 |
| 4 | L-arginine | 30 ppm full scale | 97 | 86 | 6 | 61 |
| 5 | L-threonine | 30 ppm full scale | 94 | 86 | 22 | 85 |
| 6 | L-methionine | 50 ppm full scale | 96 | 77 | 2 | 31 |

(*)expressed as: ppm phosphonate needed for 100% BaSO$_4$ scale inhibition; or % scale inhibition for 100 ppm phosphonate.
(**)expressed in ppm.

A series of the aminoacid phosphonates were tested for thermal stability thereby using the method set forth above. The testing results were as follows.

| Example N° | Amino Acid | Thermal Stability at 140° C. 1 week Decomposition in % |
|---|---|---|
| 7 | L-phenylalanine | 4.3 |
| 8 | D,L-leucine | 2.9 |
| 9 | L-isoleucine | 32.3 |
| 10 | L-arginine | 18.4 |
| 11 | L-methionine | 6.5 |

The invention claimed is:

1. A method of inhibiting scale formation in water using an aminoacid alkyphosphonic acid compound having the general formula:

A-(B)$_x$ wherein A is an α-amino acid moiety selected from the group of: arginine; histidine; isoleucine; leucine; methionine; threonine; and phenylalanine; and wherein B is an alkyiphosphonic acid moiety having from 1 to 6 carbon atoms in the alkyl group;

with the proviso that x is an integer of from 1 to 6 in the event the amino acid moiety is arginine and from 1 to 3 in the event the amino acid moiety is histidine and x is 2 in the event the amino acid moiety is selected from leucine, isoleucine, methionine, threonine and phenylalanine in scale forming water systems containing more than 100 mg barium and/or strontium and/or calcium carbonate hardness per liter, said systems having a pH between 2 and 10, whereby from 0.1 to 800 ppm of the aminoacid alkyiphosphonic acid scale inhibitor are added to the scale forming water system.

2. The method in accordance with claim 1 wherein of from 0.2 to 100 ppm of the aminoacid alkylphosphonic acid scale inhibitor is added to the scale forming water system.

3. A method for oil recovery by injecting into marine oil wells an aqueous solution of an aminoacid phosphonic acid compound having the general formula:

$A\text{-}(B)_x$ wherein A is an α-amino acid moiety selected from the group of: arginine; histidine; isoleucine; leucine; methionine; threonine; and phenylalanine; and wherein B is an alkylphosphonic acid moiety having from 1 to 6 carbon atoms in the alkyl group;

with the proviso that x is an integer of from 1 to 6 in the event the amino acid moiety is arginine and from 1 to 3 in the event the amino acid moiety is histidine and x is 2 in the event the amino acid moiety is selected from leucine, isoleucine, methionine, threonine and phenylalanine in a level of from 0.1 to 100000 ppm.

4. The method for oil recovery in accordance with claim 3 wherein an aqueous solution containing of from 0.1 to 800 ppm of the aminoacid phosphonic acid compound is continuously injected into the well.

5. The method of oil recovery in accordance with claim 3 comprising, in sequence: stopping the production wellbore activity; introducing through the production wellbore the aqueous treatment solution comprising the aminoacid phosphonic acid scale inhibitor in a level of from 100 to 100000 ppm; injecting sea water through the production wellbore to place the scale inhibitor within the targeted area of the formation; restarting the oil extraction activity; and producing return fluids, containing oil and return water, through the production wellbore.

6. The method in accordance with any one of claims 3, 4 and 5 wherein the amino acid moiety in the alkylphosphonic acid compound is selected from the group of:
 -L-phenylalanine;
 -D,L-leucine;
 -L-histidine; and
 -L-methionine ;
 whereby x is 2 in each of such species.

7. The method in accordance with any one of claims 3, 4 and 5 whereby in the event a mixture of scale inhibitors is used a single one of the amino acid alkylphosphonic acid scale inhibitors shall constitute, on a ponderal basis, 60% by weight or more of the total scale inhibitors.

8. The method in accordance with any one of claims 3, 4 and 5 wherein the scale inhibitor has a thermal stability, measured at 140 ° C., of at least about 90% by weight, whereby the amino acid moiety in said scale inhibitor is selected from the group of L-phenylalanine, D,L-leucine and L-methionine said amino acid moieties being attached to two alkylphosphonic acid moieties.

9. The method in accordance with any one of claims 1 and 3 wherein, in addition to the amino acid alkylphosphonic acid scale inhibitor, a polylphosphonic acid is present, said polyphosphonic acid being selected from the group of:
 (a) aminopolyalkylene polyphosphonic acid whereby the alkylene moiety contains from 1 to 20 carbon atoms;
 (b) hydroxyalkylene polyphosphonic acids wherein the alkylene moiety contains from 2 to 50 carbon atoms; and
 (c) phosphono alkane polycarboxylic acids wherein the alkane moiety is in straight chain configuration containing from 3 to 12 carbon atoms;
 in a ponderal ratio of amino acid alkyl phosphonic acid to polyphosphonic acid in the range of from 98:2 to 25:75.

10. The method in accordance with claim 9 wherein the polyphosphonic acid is selected from: amino tri (methylene phosphonic acid) and its N-oxide; ethylenediamine tetra (methylene phosphonic acid); diethylene triamine penta (methylenephosphonic acid); hexamethylene diamine tetra (methylene phosphonic acid); hydroxyethyl aminobis (methylene phosphonic acid); N, N'-bis (3-aminopropyl) -ethylenediamine hexa (methylene phosphonic acid); and butane-2-phosphono-1, 2, A-tricarboxylic acid,
 wherein the ponderal ratio of amino acid phosphonate to phosphonic acid is in the range of from 90:10 to 50:50.

* * * * *

UNITED STATES PATENT AND TRADEMARK OFFICE
CERTIFICATE OF CORRECTION

PATENT NO. : 8,505,626 B2  Page 1 of 1
APPLICATION NO. : 12/376899
DATED : August 13, 2013
INVENTOR(S) : Notte et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 252 days.

Signed and Sealed this
Fifteenth Day of September, 2015

Michelle K. Lee
*Director of the United States Patent and Trademark Office*